United States Patent
Johns et al.

(10) Patent No.: US 8,183,372 B2
(45) Date of Patent: May 22, 2012

(54) SUBSTITUTED 9,11-DIOXO-2,3,4A,5,9,11,13, 13A-OCTAHYDOR-1H-PYRIDO[1,2-A]-PYRROLO-[1',2':3,4]IMIDAZO[1,2-D]-PYRAZINES

(75) Inventors: Brian Alvin Johns, Research Triangle Park, NC (US); Yasunori Aoyama, Osaka (JP); Hiroshi Yoshida, Osaka (JP); Yoshiyuki Taoda, Osaka (JP)

(73) Assignees: Shionogi & Co., Ltd., Osaka (JP); GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/055,046

(22) PCT Filed: Jul. 23, 2009

(86) PCT No.: PCT/US2009/051501
§ 371 (c)(1),
(2), (4) Date: Jan. 20, 2011

(87) PCT Pub. No.: WO2010/011816
PCT Pub. Date: Jan. 28, 2010

(65) Prior Publication Data
US 2011/0124598 A1 May 26, 2011

Related U.S. Application Data

(60) Provisional application No. 61/083,603, filed on Jul. 25, 2008.

(51) Int. Cl.
*C07D 241/36* (2006.01)
(52) U.S. Cl. .......... 544/343
(58) Field of Classification Search .......... 544/343
See application file for complete search history.

(56) References Cited

U.S. PATENT DOCUMENTS

| | | |
|---|---|---|
| 2007/0072831 A1 | 3/2007 | Cai et al. |
| 2007/0161653 A1 | 7/2007 | Gudmundsson et al. |

FOREIGN PATENT DOCUMENTS

WO 2006/116764 11/2006

OTHER PUBLICATIONS

Supplementary European Search Report issued Jul. 19, 2011 in European Application No. 09800993.9.

M. Safadi et al., "Phosphoryloxymethyl Carbamates and Carbonates—Novel Water-Soluble Prodrugs for Amines and Hindered Alcohols", Pharmaceutical Research, vol. 10, No. 9, pp. 1350-1355, Sep. 1, 1993.

International Search Report issued Oct. 9, 2009 in International (PCT) Application No. PCT/US2009/051501 along with the Written Opinion.

*Primary Examiner* — James O Wilson
*Assistant Examiner* — Douglas M Willis
(74) *Attorney, Agent, or Firm* — Wenderoth, Lind & Ponack, L.L.P.

(57) ABSTRACT

The present invention is directed to a process for the preparation of a compound of formula 1b

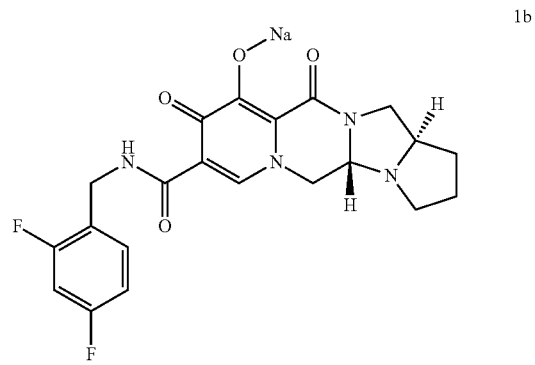

which compound is useful as a prodrug of HIV integrase inhibitors and therefore is useful in the inhibition of HIV replication, the prevention and/or treatment of infection by HIV, and in the treatment of AIDS and/or ARC. The process includes the steps of a) brominating a compound of formula P-7 to form a compound of formula P-8, b) treating a compound of formula P-8 with $NaIO_4$ to form a compound of formula P-9, c) reacting a compound of formula P-9 with [(2R)-pyrrolidinylmethyl]amine of formula to form a compound of formula P-10, d) reacting a compound of formula P-10 with 2, 4-difluorobenzylamine to form a compound of formula P-11, e) treating a compound of P-11 with palladium on carbon and ammonium hydroxide to form a compound of formula 1a, and f) treating a compound of formula 1a with NaOH and ethanol to form a compound of formula 1b. The structures of the above mentioned compounds are disclosed in the specification.

1 Claim, 1 Drawing Sheet

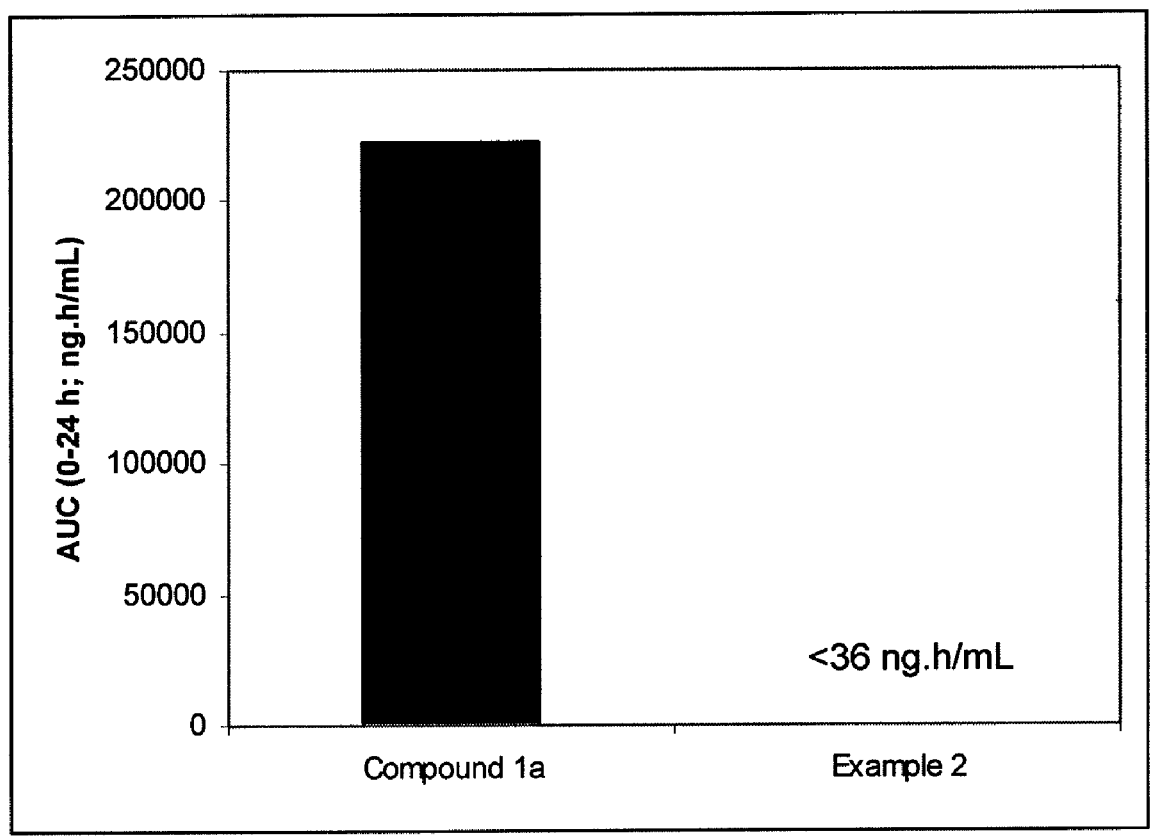

SUBSTITUTED 9,11-DIOXO-2,3,4A,5,9,11,13, 13A-OCTAHYDOR-1H-PYRIDO[1,2-A]-PYRROLO[1',2':3,4]IMIDAZO[1,2-D]-PYRAZINES

CROSS-REFERENCE TO RELATED APPLICATIONS

This application is a U.S. national stage of International Application No. PCT/US2009/051501 filed Jul. 23, 2009, which claims the benefit of U.S. application Ser. No. 61/083,603 filed Jul. 25, 2008.

BACKGROUND OF THE INVENTION

FIELD OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

A required step in HIV replication in human T-cells is the insertion by virally-encoded integrase of proviral DNA into the host cell genome. Integration is believed to be mediated by integrase in a process involving assembly of a stable nucleoprotein complex with viral DNA sequences, cleavage of two nucleotides from the 3' termini of the linear proviral DNA and covalent joining of the recessed 3' OH termini of the proviral DNA at a staggered cut made at the host target site. The repair synthesis of the resultant gap may be accomplished by cellular enzymes.

DESCRIPTION OF RELATED ART

There is continued need to find new therapeutic agents to treat human diseases. HIV integrase is an attractive target for the discovery of new therapeutics due to its important role in viral infections, particularly HIV infections. Integrase inhibitors are disclosed in WO2006/116724. The compounds of the present invention were designed to deliver active therapeutic agents.

BRIEF SUMMARY OF THE INVENTION

The present invention features compounds that are prodrugs of HIV integrase inhibitors and therefore are useful in the inhibition of HIV replication, the prevention and/or treatment of infection by HIV, and in the treatment of AIDS and/or ARC. The present invention features a compound of formula (I):

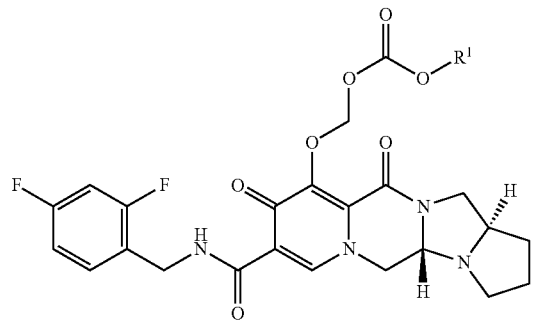

wherein:
$R^1$ is $C_1$-$C_8$alkyl or $LR^2$;
L is alkylene;
$R^2$ is
a) hydroxy;
b) alkoxy;
c) $OR^3$ wherein $R^3$ is $P(O)(OH)_2$ or alkoxy;
d) heterocyclyl optionally substituted with oxo or $C_1$-$C_8$ alkyl;
e) $C(O)OR^4$ wherein $R^4$ is H, $C_1$-$C_8$ alkyl, or $XR^5$ wherein X is alkylene and $R^5$ is $C_6$-$C_{10}$ aryl, heterocyclyl, or $NR^6R^7$ wherein $R^6$ and $R^7$ are independently selected from the group consisting of H and $C_1$-$C_8$alkyl;
f) $NR^6R^7$;
g) $C(O)NR^8R^9$ wherein $R^8$ and $R^9$ are independently selected from the group consisting of H and $XR^5$; or
h) $C(O)R^{10}$ wherein $R^{10}$ is heterocyclyl optionally substituted with $XR^{11}$ wherein $R^{11}$ is heterocyclyl;
or a pharmaceutically acceptable salt thereof.

BRIEF DESCRIPTION OF THE DRAWINGS

FIG. 1: Plasma concentrations (4aS,13aR)-N-[(2,4-Difluorophenyl)methyl]-10-hydroxy-9-11-dioxo-2,3,4a,5,9,11,13,13a-octahydro-1-H-pyrido[1,2-a]pyrrolo[1',2',3,4]imidazo[1,2-d]pyrazine-8-carboxamide (Compound 1a of Scheme 2) and a prodrug, Example 2.

DETAILED DESCRIPTION OF THE INVENTION

The present invention includes the compounds of Formula (I), useful in delivering therapeutic agents for treating or preventing viral infections, particularly HIV infections, pharmaceutical compositions comprising compounds of Formula (I), and processes for preparing the compounds.

The present invention features a compound of formula (I):

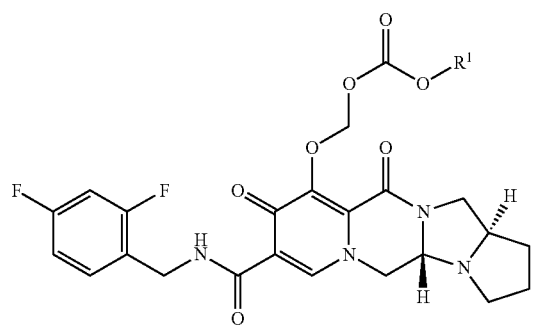

wherein:
$R^1$ is $C_1$-$C_8$alkyl or $LR^2$;
L is alkylene;
$R^2$ is
a) hydroxy;
b) alkoxy;
c) $OR^3$ wherein $R^3$ is $P(O)(OH)_2$ or alkoxy;
d) heterocyclyl optionally subsituted with oxo or $C_1$-$C_8$alkyl;
e) $C(O)OR^4$ wherein $R^4$ is H, $C_1$-$C_8$ alkyl, or $XR^5$ wherein X is alkylene and $R^5$ is $C_6$-$C_{10}$aryl, heterocyclyl, or $NR^6R^7$ wherein $R^6$ and $R^7$ are independently selected from the group consisting of H and $C_1$-$C_8$alkyl;
f) $NR^6R^7$;
g) $C(O)NR^8R^9$ wherein $R^8$ and $R^9$ are independently selected from the group consisting of H and $XR^5$; or
h) $C(O)R^{10}$ wherein $R^{10}$ is heterocyclyl optionally substituted with $XR^{11}$ wherein $R^{11}$ is heterocyclyl;
or a pharmaceutically acceptable salt thereof.

The present invention features a compound of formula (I) wherein $R^1$ is $LR^2$ wherein $R^2$ is $OR^3$ or $C(O)OR^4$.

The present invention features a compound of formula (I) wherein $R^1$ is $LR^2$ wherein $R^2$ is $OR^3$ or $C(O)OR^4$ wherein $R^3$ is $P(O)(OH)_2$ and $R^4$ is $XR^5$ wherein X is alkylene and $R^5$ is $C_{6-10}$ aryl.

The present invention also features a compound selected from the group consisting of:
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl methyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(methyl)ethyl carbonate;
Methyl ({[({[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl)oxy]carbonyl}oxy)acetate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(4-morpholinyl)ethyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-hydroxyethyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(phosphonooxy)ethyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-hydroxypropyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-hydroxypropyl carbonate;
{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-(phosphonooxy)propyl carbonate;
and pharmaceutically acceptable salts thereof.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkylene" refers to a straight or branched chain divalent hydrocarbon radical, preferably having from one to twelve carbon atoms, unless otherwise defined. Examples of "alkylene" as used herein include, but are not limited to, methylene, ethylene, propylene, butylene, isobutylene and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl" alone or in combination with any other term, refers to a carbocyclic aromatic moiety (such as phenyl or naphthyl) containing the specified number of carbon atoms, preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "heterocycle," "heterocyclic," and "heterocyclyl" as used herein, refer to a 3- to 7- membered monocyclic heterocyclic ring or 8-to 11- membered bicyclic heterocyclic ring system any ring of which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results. "Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle, "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle," "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroatom" means nitrogen, oxygen, or sulfur and includes any oxidized form of nitrogen, such as N(O) {N$^+$-O$^-$} and sulfur such as S(O) and S(O)$_2$, and the quaternized form of any basic nitrogen.

A combination of substituents or variables is permissible only if such a combination results in a stable or chemically feasible compound.

Unless otherwise stated, structures depicted herein are also meant to include all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. Treatment includes prophylaxis which refers to preventing a disease or condition or preventing the occurrence of symptoms of such a disease or condition, in a patient. As used herein, the term "patient" refers to a mammal, including a human.

As used herein, the term "subject" refers to a patient, animal or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, NW$_4^+$ (wherein W is C$_{1-4}$ alkyl) and other amine salts. Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with, a hydroxy group include the anion of said compound in combination with a suitable cation such as Na$^+$, NH$_4^+$, and NW$_4^+$ (wherein W is a C$_{1-4}$alkyl group). Preferred salts include sodium, calcium, potassium, and hydrochloride.

Other compounds of this invention may be prepared by one skilled in the art following the teachings of the specification coupled with knowledge in the art using reagents that are readily synthesized or commercially available.

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Compounds of the present invention are useful as prodrugs to deliver therapeutic compounds, for examples compounds disclosed in WO2006/116764, which were demonstrated to have HIV integrase inhibitory activity. One aspect of the instant invention relates to methods of treating or preventing viral infection, for example an HIV infection, in a biological sample comprising contacting the biological sample with compounds of formula (I) or pharmaceutically acceptable salts thereof. Another aspect of the instant invention relates to methods of treating or preventing viral infection, for example, an HIV infection, in a patient comprising administering to the patient a therapeutically effective amount of compounds of formula (I) or (Ia) or pharmaceutically acceptable salts thereof.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

According to one embodiment of the invention, compounds of formula (I) or salts thereof may be formulated into compositions. In a preferred embodiment, the composition is a pharmaceutical composition, which comprises a compound of formula (I) and pharmaceutically acceptable carrier, adjuvant or vehicle. In one embodiment, the composition comprises an amount of a compound of the present invention effective to treat or prevent viral infection, for example an HIV infection, in a biological sample or in a patient. In another embodiment, compounds of this invention and pharmaceutical compositions thereof, which comprise an amount of a compound of the present innovation effective to inhibit viral replication or to treat or prevent a viral infection or disease or disorder, for example an HIV infection, and a pharmaceutically acceptable carrier, adjuvant or vehicle, may be formulated for administration to a patient, for example, for oral administration.

The present invention features compounds according to the invention for use in medical therapy, for example for the treatment or prophylaxis of a viral infection, for example an HIV infection and associated conditions. The compounds according to the invention are especially useful for the treatment of AIDS and related clinical conditions such as AIDS related complex (ARC), progressive generalized lymphadenopathy (PGL), Kaposi's sarcoma, thromobocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment or prevention of the symptoms or effects of a viral infection in an infected patient, for example, a mammal including a human, which comprises administering to said patient a pharmaceutically effective amount of a compound according to the invention. According to one aspect of the invention, the viral infection is a retroviral infection, in particular an HIV infection.

The present invention further includes the use of a compound according to the invention in the manufacture of a medicament for administration to a subject for the treatment of a viral infection, in particular and HIV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment or prophylaxis of any of the aforementioned diseases or conditions.

Reference herein to treatment extends to prophylaxis as well as the treatment of established conditions, disorders and infections, symptoms thereof, and associated. The above compounds according to the invention and their pharmaceutically acceptable salts may be employed in combination with other therapeutic agents for the treatment of the above infections or conditions. Combination therapies according to the present invention comprise the administration of a compound of the present invention or a pharmaceutically acceptable salt thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of other therapeutic agents include:

Nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, TMC-278, TMC-125, etravirine, and similar agents;

Protease inhibitors such as saquinavir, ritonavir, indinavir, nelfinavir, amprenavir, fosamprenavir, brecanavir, raltegravir, atazanavir, tipranavir, palinavir, lasinavir, and similar agents;

Entry inhibitors such as enfuvirtide (T-20), T-1249, PRO-542, PRO-140, TNX-355, BMS-806, 5-Helix and similar agents;

Integrase inhibitors such as L-870,810 and similar agents;

Budding inhibitors such as PA-344 and PA-457, and similar agents; and

CXCR4 and/or CCR5 inhibitors such as vicriviroc (Sch-C), Sch-D, TAK779, maraviroc (UK 427,857), TAK449 and similar agents.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day. Unless otherwise indicated, all weights of active ingredient are calculated as the parent compound of formula (I) for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms containing, for example, 1 to 1000 mg or 20 to 500 mg, or 10 to 500 mg, or 1 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable salt thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray. Pharmaceutical compositions may contain in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The compounds of the present invention may be prepared according to the following reactions schemes and examples, or modifications thereof using readily available starting materials, reagents and conventional synthesis procedures. In these reactions, it is also possible to make use of variants which are known to those of ordinary skill in the art.

(4aS,13aR)-N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide may be made by methods know to those skilled in the art, including methods disclosed in WO2006/116724.

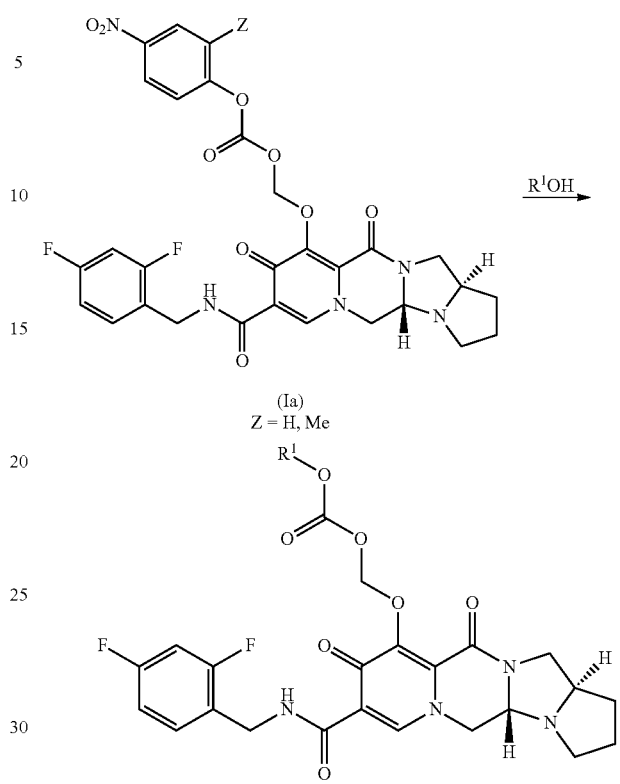

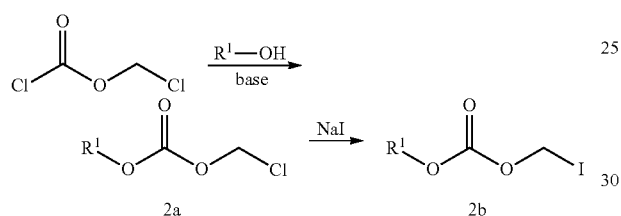

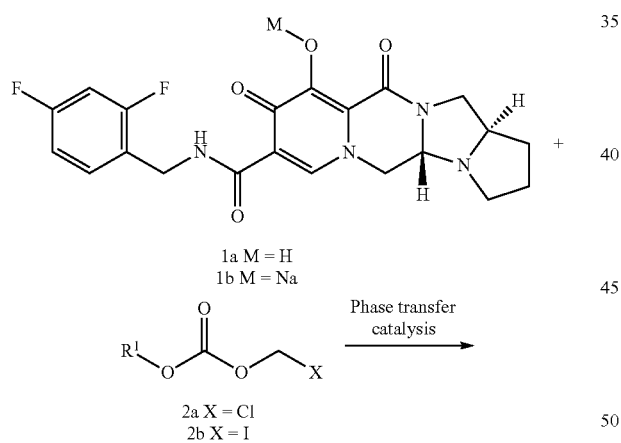

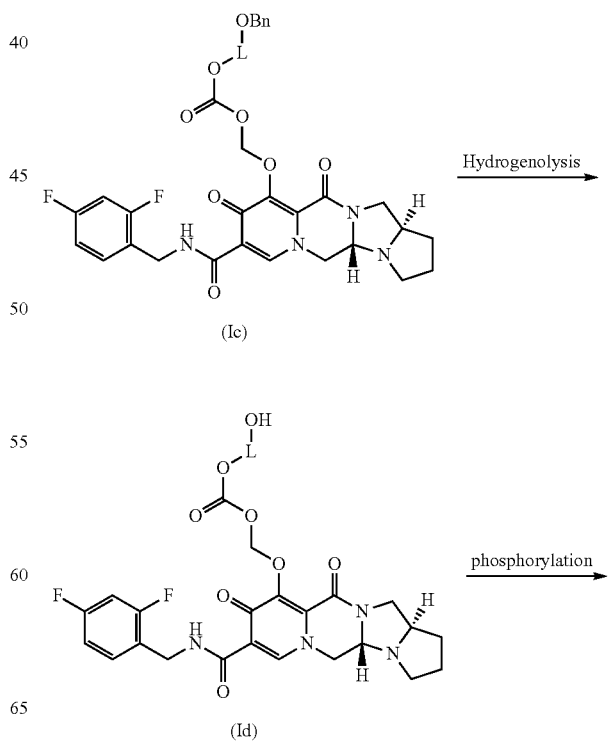

13
-continued
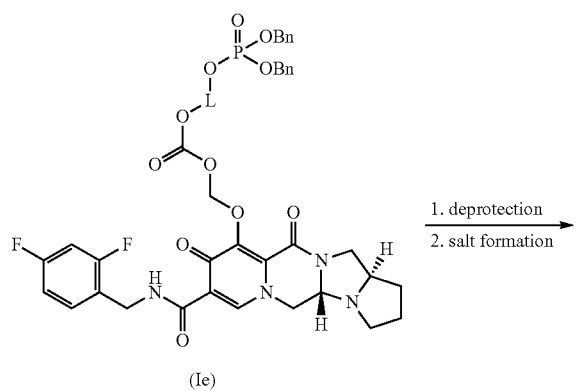
(Ie)
1. deprotection
2. salt formation
14
-continued
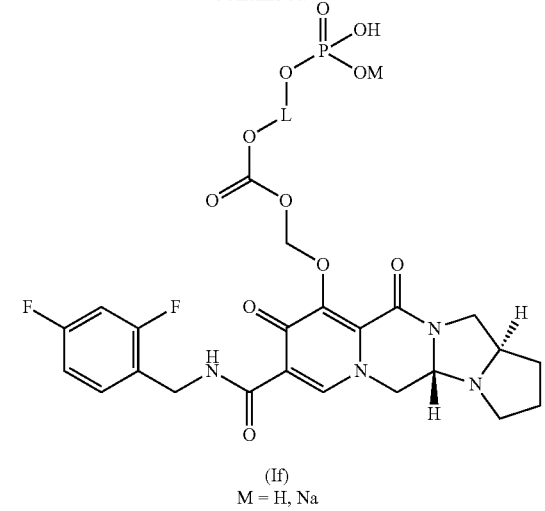
(If)
M = H, Na
Scheme 5
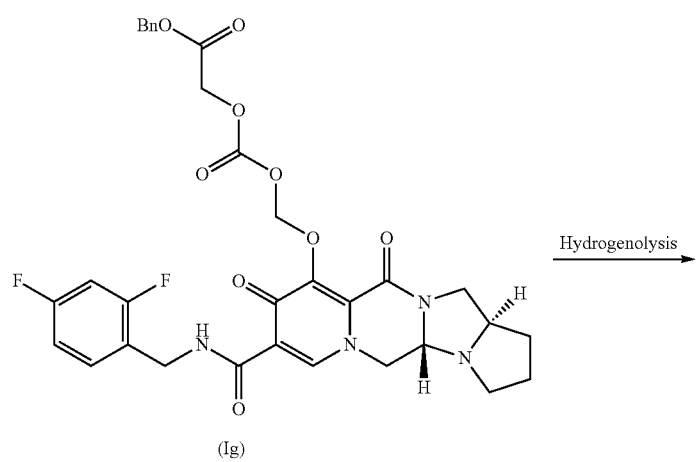
(Ig)
Hydrogenolysis
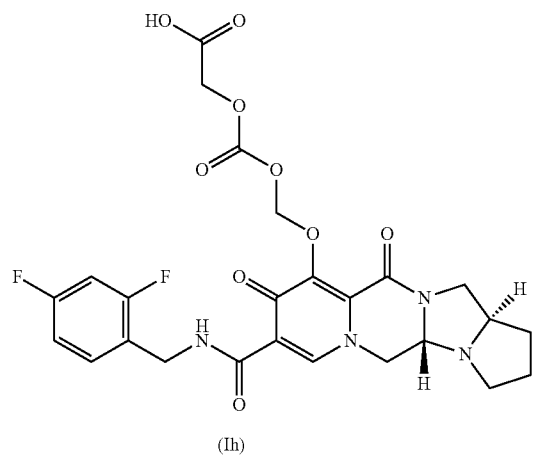
(Ih)
amine coupling        alcohol coupling

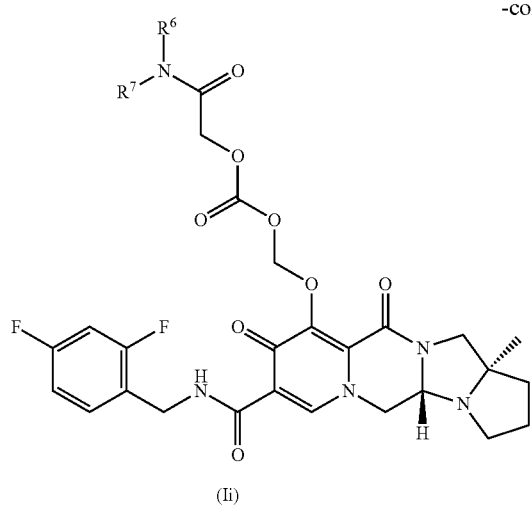
(Ii)
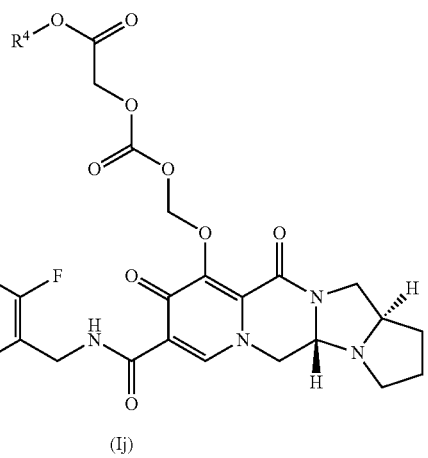
(Ij)
The following examples are intended for illustration only and are not intended to limit the scope of the invention in any way.
Preparation 1
(4aS,13aR)-N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (compound 1b, scheme 2).
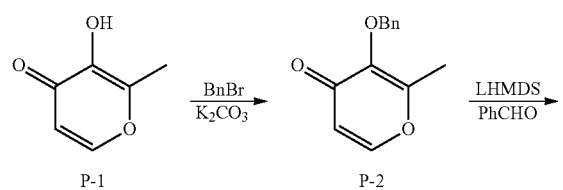
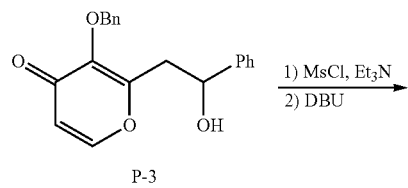
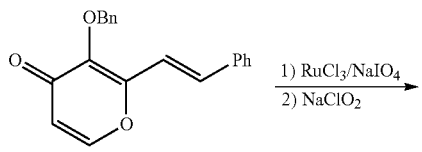
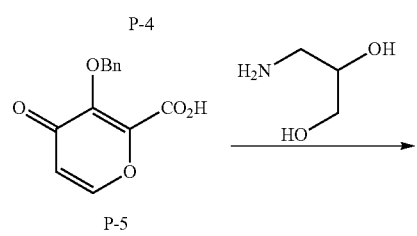
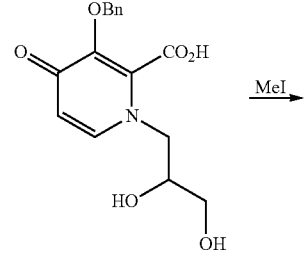
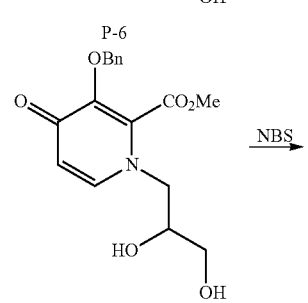
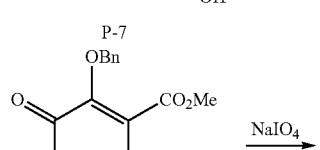
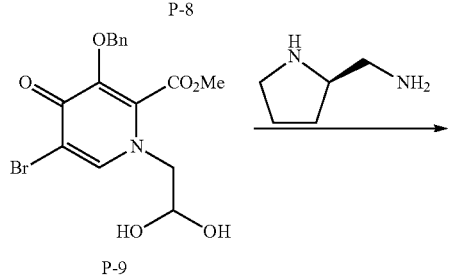

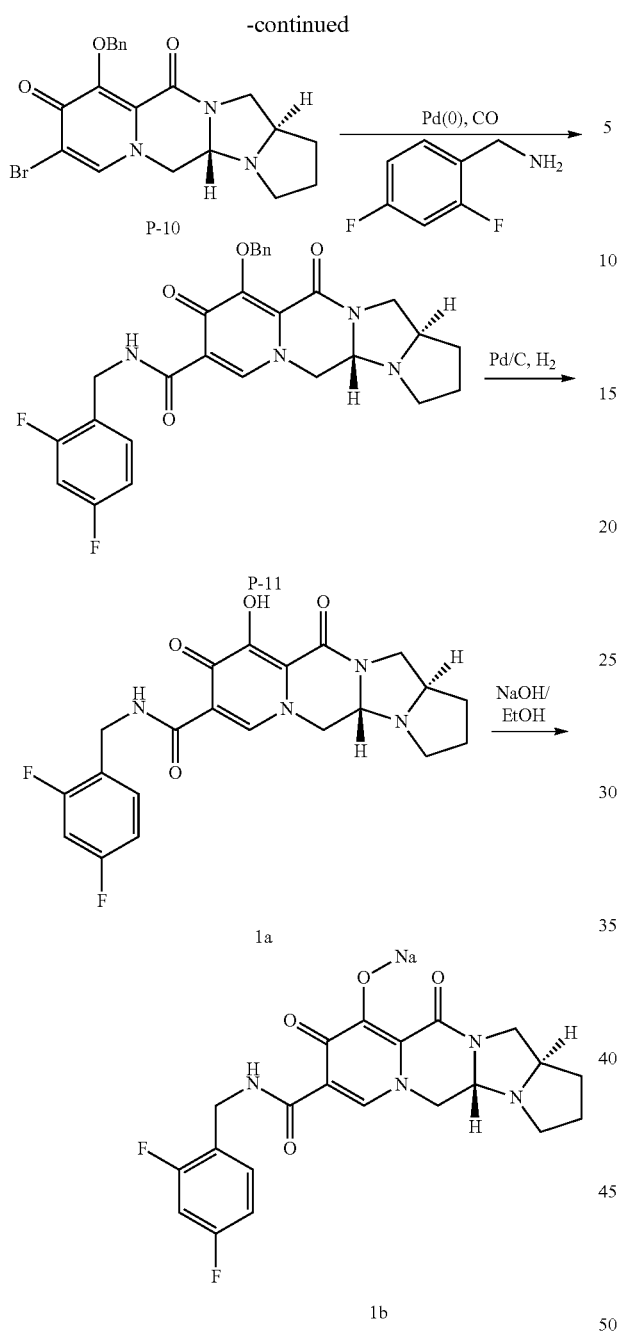

a) Synthesis of 2-methyl-3-[(phenylmethyl)oxy]-4H-pyran-4-one (compound P-2). To a slurry of 2000 g of compound P-1 (1.0 eq.) in 14.0 L of MeCN were added 2848 g of benzyl bromide(1.05 eq.) and 2630 g of K₂CO₃(1.2 eq.). The mixture was stirred at 80° C. for 5 h and cooled to 13° C. Precipitate was filtered and washed with 5.0 L of MeCN. The filtrate was concentrated and 3.0 L of THF was added to the residue. The THF solution was concentrated to give 3585 g of crude compound P-2 as oil. Without further purification, compound P-2 was used in the next step. ¹H NMR(300 MHz, CDCl₃) δ 7.60 (d, J=5.7 Hz, 1H), 7.4-7.3 (m, 5H), 6.37 (d, J=5.7 Hz, 1H), 5.17 (s, 2H), 2.09 (s, 3H).

b) Synthesis of 2-(2-hydroxy-2-phenylethyl)-3-[(phenylmethyl)oxy]-4H-pyran-4-one (compound P-3). To 904 g of the crude compound P-2 was added 5.88 L of THF and the solution was cooled to −60° C. 5.00 L of 1.0 M of Lithium bis(trimethylsilylamide) in THF(1.25 eq.) was added dropwise for 2 h to the solution of compound 2 at −60° C. Then, a solution of 509 g of benzaldehyde(1.2 eq.) in 800 mL of THF was added at −60° C. and the reaction mixture was aged at −60° C. for 1 h. The THF solution was poured into a mixture of 1.21 L of conc. HCl, 8.14 L of ice water and 4.52 L of EtOAc at less than 2° C. The organic layer was washed with 2.71 L of brine (twice) and the aqueous layer was extracted with 3.98 L of EtOAc. The combined organic layers were concentrated. To the mixture, 1.63 L of toluene was added and concentrated (twice) to provide toluene slurry of compound P-3. Filtration, washing with 0.90 L of cold toluene and drying afforded 955 g of compound P-3 (74% yield from compound P-1) as a solid. ¹H NMR(300 MHz, CDCl₃) δ 7.62 (d, J=5.7 Hz, 1H), 7.5-7.2 (m, 10H), 6.38 (d, J=5.7 Hz, 1H), 5.16 (d, J=11.4 Hz, 1H), 5.09 (d, J=11.4 Hz, 1H), 4.95 (dd, J=4.8, 9.0 Hz, 1H), 3.01 (dd, J=9.0, 14.1 Hz, 1H), 2.84 (dd, J=4.8, 14.1 Hz, 1H).

c) Synthesis of 2-[(E)-2-phenylethenyl]-3-[(phenylmethy)oxy]-4H-pyran-4-one (compound P-4). To a solution of 882 g of compound P-3 (1.0 eq.) in 8.82 L of THF were added 416 g of Et₃N (1.5 eq.) and 408 g of methanesulfonyl chloride (1.3 eq.) at less than 30° C. After confirmation of disappearance of compound P-3, 440 mL of NMP and 1167 g of DBU (2.8 eq.) were added to the reaction mixture at less than 30° C. and the reaction mixture was aged for 30 min. The mixture was neutralized with 1.76 L of 16% sulfuric acid and the organic layer was washed with 1.76 L of 2% Na₂SO3aq. After concentration of the organic layer, 4.41 L of toluene was added and the mixture was concentrated (tree times). After addition of 4.67 L of hexane, the mixture was cooled with ice bath. Filtration, washing with 1.77 L of hexane and drying provided 780 g of compound P-4 (94% yield) as a solid. ¹H NMR(300 MHz, CDCl₃) δ 7.69 (d, J=5.7 Hz, 1H), 7.50-7.25 (m, 10H), 7.22 (d, J=16.2 Hz, 1H), 7.03 (d, J=16.2 Hz, 1H), 6.41 (d, J=5.7 Hz, 1H), 5.27 (s, 2H).

d) Synthesis of 4-oxo-3-[(phenylmethyl)oxy]-4H-pyran-2-carboxylic acid (compound P-5). To a mixture of 822 g of compound P4 (1.0 eq.) and 11.2 g of RuCl₃.nH₂O (0.02 eq.) in 2.47 L of MeCN, 2.47 L of EtOAc and 2.47 L of H₂O was added 2310 g of NalO₄(4.0 eq.) at less than 25° C. After aging for 1 h, 733 g of NaClO₂(3.0 eq.) was added to the mixture at less than 25° C. After aging for 1 h, precipitate was filtered and washed with 8.22 L of EtOAc. To the filtrate, 1.64 L of 50% Na₂S₂O₃aq, 822 mL of H₂O and 630 mL of coc.HCl were added. The aqueous layer was extracted with 4.11 L of EtOAc and the organic layers were combined and concentrated. To the residue, 4 L of toluene was added and the mixture was concentrated and cooled with ice bath. Filtration, washing with 1 L of toluene and drying provided 372 g of compound P-5 (56% yield) as a solid. ¹H NMR(300 MHz, CDCl₃) δ 7.78 (d, J=5.7 Hz, 1H), 7.54-7.46 (m, 2H), 7.40-7.26 (m, 3H), 6.48 (d, J=5.7 Hz, 1H), 5.6 (brs, 1H), 5.31 (s, 2H).

e) Synthesis of 1-(2,3-dihydroxypropyl)-4-oxo-3-[(phenylmethyl)oxy]-1,4-dihydro-2-pyridinecarboxylic acid (compound P-6). A mixture of 509 g of compound P-5 (1.0 eq.) and 407 g of 3-amino-propane-1,2-diol (2.5 eq.) in 1.53 L of EtOH was stirred at 65° C. for 1 h and at 80° C. for 6 h. After addition of 18.8 g of 3-Amino-propane-1,2-diol (0.1 eq.) in 200 mL of EtOH, the mixture was stirred at 80° C. for 1 h. After addition of 18.8 g of 3-amino-propane-1,2-diol (0.1 eq.) in 200 mL of EtOH, the mixture was stirred at 80° C. for 30 min. After cooling and addition of 509 mL of $H_2O$, the mixture was concentrated. To the residue, 2.54 L of $H_2O$ and 2.54 L of AcOEt were added. After separation, the aqueous layer was washed with 1.02 L of EtOAc. To the aqueous layer, 2.03 L of 12% sulfuric acid was added at less than 12° C. to give crystal of compound P-6. Filtration, washing with 1.53 L of cold $H_2O$ and drying provided 576 g of compound P-6 (83% yield) as a solid. $^1$H NMR(300 MHz, DMSO-$d_6$) δ 7.67 (d, J=7.5 Hz, 1H), 7.5-7.2 (m, 5H), 6.40 (d, J=7.5 Hz, 1H), 5.07 (s, 2H), 4.2-4.0 (m, 1H), 3.9-3.6 (m, 2H), 3.38 (dd, J=4.2, 10.8 Hz, 1H), 3.27 (dd, J=6.0, 10.8 Hz, 1H).

f) Synthesis of methyl 1-(2,3-dihydroxypropyl)-4-oxo-3-[(phenylmethyl)oxy]-1,4-dihydro-2-pyridinecarboxylate (compound P-7). To a slurry of 576 g of compound P-6 (1.0 eq.: 5.8% of $H_2O$ was contained) in 2.88 L of NMP were added 431 g of $NaHCO_3$ (3.0 eq.) and 160 mL of methyl iodide (1.5 eq.) and the mixture was stirred at room temperature for 4 h. After cooling to 5° C., 1.71 L of 2N HCl and 1.15 L of 20% NaClaq were added to the mixture at less than 10° C. to give crystal of compound 7. Filtration, washing with 1.73 L of $H_2O$ and drying provided 507 g of compound P-7 (89% yield) as a solid. $^1$H NMR(300 MHz, DMSO-$d_6$) δ 7.59 (d, J=7.5 Hz, 1H), 7.40-7.28 (m, 5H), 6.28 (d, J=7.5 Hz, 1H), 5.21 (d, J=5.4 Hz, 1H), 5.12 (d, J=10.8 Hz, 1H), 5.07 (d, J=10.8 Hz, 1H), 4.83 (t, J=5.7 Hz, 1H), 3.97 (dd, J=2.4, 14.1 Hz, 1H), 3.79 (s, 3H), 3.70 (dd, J=9.0, 14.4 Hz, 1H), 3.65-3.50 (m, 1H), 3.40-3.28 (m, 1H), 3.26-3.14 (m, 1H).

g) Synthesis of methyl 5-bromo-1-(2,3-dihydroxypropyl)-4-oxo-3-[(phenylmethyl)oxy]-1,4-dihydro-2-pyridinecarboxylate (compound P-8). A reactor was charged with (3.759 kg, 11.27 mol) of methyl 1-(2,3-dihydroxypropyl)-4-oxo-3-[(phenylmethyl)oxy]-1,4-dihydro-2-pyridinecarboxylate (P-7) and 18.8 L of DMF. To this agitated mixture at 18-20° C. was added N-bromosuccinimide (2.220 kg, 12.47 mol) over 20 minutes via a powder funnel. The resultant mixture was stirred at rt for 16 h. At this time less than 1% of starting material was present by HPLC. The mixture was worked up in half batches by cooling to 10° C. and added an ice/water mixture (12 kg ice in 35 kg deionized water) and the mixture was agitated, then filtered. This was repeated for the second half of the batch. The combined filter cake was washed with 14 L of water and dried in a vacuum oven to provide 4.033 kg of methyl 5-bromo-1-(2,3-dihydroxypropyl)-4-oxo-3-[(phenylmethyl)oxy]-1,4-dihydro-2-pyridinecarboxylate P-8 (91.6%) as an off-white powder of 99.2% HPLC purity. $^1$H NMR(300 MHz, Methanol-$d_4$) δ 8.21 (s, 1 H), 7.41-7.33 (m, 5 H), 5.16 (s, 2H), 4.17 (dd, J=14.3, 2.4 Hz, 1 H), 3.90 (dd, J=14.3, 9.0 Hz, 1 H), 3.81 (s, 3 H), 3.78 (m, 1), 3.52 (dd, J=11.3, 4.8 Hz, 1 H), 3.41 (dd, J=11.3, 6.3 Hz, 1 H).

h) Synthesis of methyl 5-bromo-1-[2-hydroxy-2-(methyl)ethyl]-4-oxo-3-[(phenylmethypoxy]-1,4-dihydro-2-pyridinecarboxylate (compound P-9) in equilibrium with the corresponding aldehyde). A reactor was charged with sodium periodate (1.67 kg, 7.8 mol) and 44 L of deionized water. To the agitated mixture was added 8.5 kg of ice. This was stirred until all the ice melted and the mixture temperature was 1.4° C. To this was added methyl 5-bromo-1-(2,3-dihydroxypropyl)-4-oxo-3-[(phenylmethypoxy]-1,4-dihydro-2-pyridinecarboxylate P-8 (2.73 kg, 6.62 mol) via a powder addition funnel. The mixture was allowed to warm to rt and the slurry was stirred for 16 h. A sample was monitored by $^1$H NMR and showed the disappearance of starting material. The mixture was filtered and the cake washed with 20 kg of deionized water. This was repeated until a negative starch/iodide paper result was obtained (4×20 L washes). The solids were dried in a vacuum oven at 45-55° C. to provide methyl 5-bromo-1-(2,2-dihydroxyethyl)-4-oxo-3-[(phenylmethypoxy]-1,4-dihydro-2-pyridinecarboxylate P-9 (2.176 kg, 88%) as a mixture with the corresponding aldehyde form. Purity was determined to be 99.5% by HPLC. $^1$H NMR(300 MHz, acetone-$d_6$) δ 8.12 (s, 1 H), 7.49-7.30 (m, 5 H), 5.56 (dd, J=6.0, 2.4 Hz, 1 H), 5.23 (m, 1 H), 5.20 (s, 2 H), 3.97 (d, J=5.1 Hz, 2 H), 3.87 (s, 3 H).

i) Synthesis of (4aS,13aR)-8-bromo-10-[(phenylmethypoxy]-2,3,4a,5,13,13a-hexahydro-1H-pyrido[1,2-a]pyrrolo[1',2':3,4]imidazo[1,2-d]pyrazine-9,11-dione (DD). A reactor was charged with [(2R)-2-pyrrolidinylmethyl]amine (0.75 kg) and 4.6 L of DMF was added followed by 0.45 kg of glacial acetic acid. Acetonitrile (41.4 L) was then added and the mixture was agitated for 15 minutes. To the reaction mixture was added methyl 5-bromo-1-(2,2-dihydroxyethyl)-4-oxo-3-[(phenylmethyl)oxy]-1,4-dihydro-2-pyridinecarboxylate (P-9) (2.30 kg). After stirring for 20 minutes at ambient temperature, the mixture was heated at 75-85° C. until the bromide starting material was consumed by HPLC analysis (about 6 hrs). Upon completion, the mixture was cooled until the reflux subsided and then charged with 6.9 L of methanol and the mixture was heated at reflux for about 45 minutes then cooled to 15° C. and filtered and dried to provide P-10 (1.93 kg, 78%) as a white solid. $^1$H NMR (300 MHz, DMSO-$d_6$) δ ppm 8.65 (m, 1 H), 7.54 (m, 2 H), 7.33 (m, 3 H), 5.15 (d, 1 H), 4.99 (d, 1 H), 4.60 (m, 1 H), 4.36 (m, 1 H), 4.03 (m, 1 H), 3.90 (m, 1 H), 3.65 (m, 1 H), 3.06-2.84 (m, 3 H), 1.92-1.60 (m, 4 H).

j) Synthesis of (4aS,13aR)-N-[(2,4-difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (compound P-11). A reaction vessel was charged with (4aS,13aR)-8-bromo-10-[(phenylmethyl)oxy]-2,3,4a,5,13,13a-hexahydro-1H-pyrido[1,2-a]pyrrolo[1',2':3,4]imidazo[1,2-d]pyrazine-9,11-dione (P-10) (1.4 kg), 2,4-difluorobenzylamine (705 g), Hunigs base (1.4 L), dppf (60 g) and DMSO (12 L). The mixture was degassed with high purity nitrogen 4 times. To this mixture was added palladium (II) trifluoroacetate (18 g) in DMSO (2L). The mixture was again degassed 3 times with high purity nitrogen and then purged with CO 3 times and left under a 45 psi atmosphere of CO. The mixture was heated at 80° C. under 45 psi CO until the reaction appeared complete by HPLC (24 hrs). The mixture was cooled to rt and slowly transferred to an ice slurry of ammonium chloride. The mixture was filtered and washed with water and isopropanol. The residue was recrystallized from isopropanol to provide (4aS,13aR)-N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (P-11) (952 g, 56%). Recrystallization of the mother liquor from isopropanol produced a second crop of crystals of the desired product in the amount of 327 g (19%). $^1$H NMR (300 MHz, DMSO-$d_6$) δ ppm 10.44 (m, 1 H), 8.55 (s, 1 H), 7.56-7.07 (m, 8 H), 5.18 (d, 1 H), 5.03 (d, 1 H), 4.62-4.54 (m, 4 H), 4.06-3.60 (m, 3 H), 3.20-2.80 (m, 3 H), 1.93-1.60 (m, 4 H).

k) Synthesis of (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide (compound 1a). A pressure reaction vessel was charged with (4aS,13aR)-N-[(2,4-Difluorophenyl)methyl]-9,11-dioxo-10-[(phenylmethyl)oxy]-2,3,4a,5,9,11,13,13a-octahydro-1H-pyrido[1,2-a]pyrrolo[1',2':3,4]imidazo[1,2-d]pyrazine-8-carboxamide (P-11) (950 g), 192 g of palladium on carbon (50% wet), ethanol (9.5 L) and concentrated ammonium hydroxide (124 mL). The mixture was degassed with nitrogen 3 times and then placed under 50 psi of hydrogen until the reaction was complete. The mixture was degassed again with nitrogen and then filtered through Celite. The cake was extracted with refluxing dichloromethane and then filtered again. The combined filtrates were concentrated to a small volume (4 L), azeotroped with ethanol (28.5 L) to a final volume of 9 L. The slurry was filtered and washed with ethanol and dried to produce (4aS,13aR)-N-[(2,4-difluorophenyl)methyl]-10-hydroxy-9,11-dioxo-2,3,4a,5,9,11,13,13a-octahydro-1 H-pyrido[1,2-a]pyrrolo[1',2':3,4]imidazo[1,2-d]pyrazine -8-carboxamide (1a) (616 g, 78.4%) as a white solid. $^1$H NMR (300 MHz, DMSO-$d_6$) δ ppm 10.37 (m, 1 H), 8.42 (s, 1 H), 7.41-7.05 (m, 3 H), 4.72-4.53 (m, 4 H), 4.05 (m, 1 H), 3.86 (m, 1 H), 3.70 (m, 1 H), 3.16 (m, 1 H), 2.88 (m, 2 H), 1.92-1.60 (m, 4 H).

l) Synthesis of (4aS,13aR)-N-[(2,4-difluorophenyl)methyl]-10-hydroxy-9,11-dioxo-2,3,4a,5,9,11, 13,13a-octahydro-1H-pyrido[1,2-a]pyrrolo[1',2':3,4]imidazo[1,2-d]pyrazine-8-carboxamide sodium salt (compound 1b). A 12-L reactor equipped with a high-torque overhead stirrer and a 19-mm stirring shaft was charged with compound 1a (666 g, 1.55 mol) and EtOH (10 L). While stirring, a 50% aqueous solution of NaOH (65 g, 87 mL, 1.62 mol, 1.05 equiv) was added over a period of 20 minutes. The mixture was vigorously stirred for 14 hours and then filtered. The filter cake was washed with EtOH (2×1.4 L) and then dried at 40° C. under high vacuum to a constant weight to afford 760 g (97%) of compound 1b as an off-white powder. The material contained 1.2 equivalents of EtOH by $^1$H NMR with a HPLC purity of >99% (AUC). This crude product was then carried forward into the water slurry. A 20-L reactor equipped with a high-torque overhead stirrer and a 19-mm stirring shaft was charged with compound 1b·1.2EtOH (740 g, 1.45 mol). Water (15 L) was added and the mixture was vigorously stirred overnight and then filtered. The filter cake was washed with water (2×1.5 L) and then dried at 40-50° C. under high vacuum to a constant weight to afford 605 g (92%) of 1b as a white solid with a purity of 99.8%. Spectral data was consistent with that previously reported in WO2006/116724 as $^1$H NMR (D$_2$O) δ 7.85 (s, 1 H), 7.23 (m, 1 H), 6.82 (m, 2 H), 4.51-4.46 (m, 3 H), 4.28 (m, 1 H),3.95 (m, 1 H), 3.84 (m, 1 H), 3.62 (m, 1 H), 3.16 (m, 1 H), 2.89 (m, 1 H), 2.84 (m, 1H), 1.90 (m, 2 H), 1.73 (m, 1 H), 1.60 (m, 1 H). ES$^+$ MS: 431 (M+1).

EXAMPLE 1

{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl methyl carbonate.

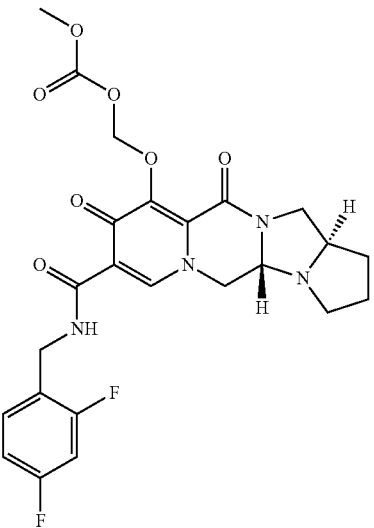

a) Chloromethyl methyl carbonate. Chloromethyl chloridocarbonate (3 ml, 33.7 mmol) was dissolved in dichloromethane (10 mL) and cooled to 0° C. Methanol (1.36 mL, 33.7 mmol) was added dropwise, followed by pyridine (2.73 mL, 33.7 mmol) dropwise. The white suspension was stirred at 0° C. and allowed to warm to ambient temperature and stirred for 14 hours. The suspension was quenched with water, diluted with aqueous citric acid, extracted with dichloromethane, washed with sodium bicarbonate, brine, dried over sodium sulfate and concentrated under reduced pressure to give chloromethyl methyl carbonate as a clear colorless oil. $^1$H NMR (CDCl$_3$) δ 5.72 (s, 2 H), 3.96 (s, 3 H).

b) Iodomethyl methyl carbonate. Chloromethyl methyl carbonate (2.05 g, 16.46 mmol) was dissolved in acetone and sodium iodide (3.70 g, 24.69 mmol) was added and the reaction was heated at 40° C. for 15 hours. The yellow suspension was allowed to cool to ambient temperature, concentrated under reduced pressure, diluted with water and aqueous sodium thiosulfate, extracted with dichloromethane, washed with brine, dried over sodium sulfate, and concentrated under reduced pressure to give iodomethyl methyl carbonate as a clear yellow oil. $^1$H NMR (CDCl$_3$) δ 5.92 (s, 2 H), 3.93 (s, 3 H).

c) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl methyl carbonate. (4aS, 13aR)-N-[(2,4-Difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (800 mg, 1.77 mmol) and potassium carbonate (733 mg, 5.31 mmol) were suspended in water and tetrabutylammonium hydrogen sulfate (600 mg, 1.77 mmol) was added followed by dichloromethane. Stirring 5 min gave a clear biphasic solution. Iodomethyl methyl carbonate (815 mg, 3.77 mmol) was added as a solution in dichloromethane. After 1 hour additional iodomethyl methyl carbonate was added and after several hours reaction was diluted with water, dichlormethane, extracted with dichlormethane, washed with sodium bicarbonate, brine, dried over sodium sulfate, and purified by silica-gel chromatography (1-12% methanol/dichloromethane gradient elution) to give the title compound. The isolated product was dissolved in dichloromethane, water was added, and the organic solvent was removed under reduced pressure until precipitation occurred. The aqueous liquid was decanted and the solid was washed several times with water. Dichlormethane was added and the the organics were washed with water and dried over sodium sulfate. Recrystalization from ethyl acetate/hexanes gave the title compound as a white crystalline solid. $^1$H NMR (CDCl$_3$) δ 10.33 (m, 1 H), 8.45 (s, 1 H), 7.32 (m, 1 H), 6.80 (m, 2 H), 5.94 (d, J=6.4 Hz, 1 H), 5.81 (d, J=6.4 Hz, 1 H), 4.61-4.55 (m, 3 H), 4.36-4.23 (m, 2 H), 4.00 (m, 1 H), 3.87 (m, 1 H), 3.80 (s, 3 H), 3.24 (m, 1 H), 3.11 (m, 1 H), 2.89 (m, 1 H), 2.10-1.94 (m, 3 H), 1.72 m, 1 H). ES$^+$ MS: 519 (M+1).

EXAMPLE 2

{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(methyl)ethyl carbonate.

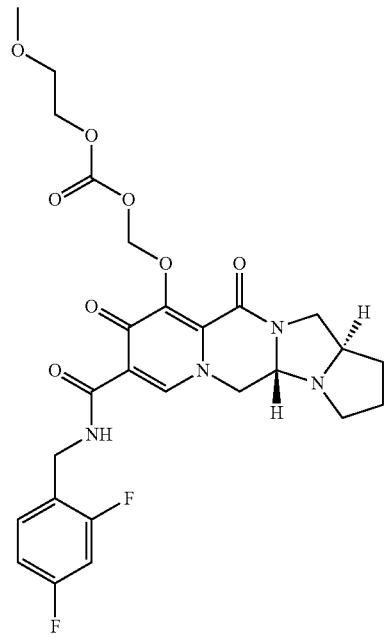

The title compound was prepared from iodomethyl 2-(methyl)ethyl carbonate (92 mg, 0.354 mmol), (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (80 mg, 0.177 mmol), potassium carbonate (73 mg, 0.531 mmol), and tetrabutylammonium hydrogen sulfate (60 mg, 0.177 mmol), using a similar process to that described in example 1. $^1$H NMR (CDCl$_3$) δ 10.23 (m, 1 H), 8.39 (s, 1 H), 7.30 (m, 1 H), 6.77 (m, 2 H), 5.89 (d, J=6.4 Hz, 1 H), 5.78 (d, J=6.4 Hz, 1 H), 4.56-4.48 (m, 3 H), 4.34-4.15 (m, 4 H), 3.86 (m, 1 H), 3.69-3.55 (m, 3 H), 3.31 (s, 3 H), 3.11-2.95 (m, 2 H), 2.78 (m, 1 H), 2.04-1.84 (m, 3 H), 1.63 (m, 1 H). ES$^+$ MS: 563 (M+1).

EXAMPLE 3

Methyl ({[({[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[2-d]pyrazin-10-yl]oxy}methyl)oxy]carbonyl}oxy)acetate.

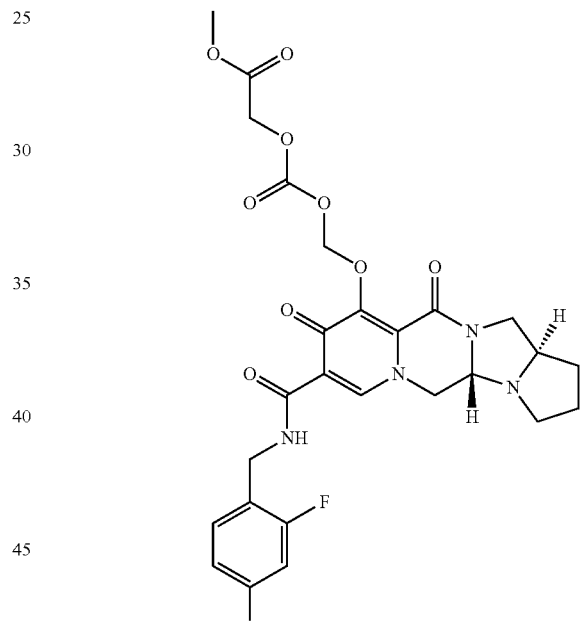

The title compound was prepared from methyl ({[(iodomethyl)oxy]carbonyl}oxy)acetate (excess), (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (80 mg, 0.177 mmol), potassium carbonate (73 mg, 0.531 mmol), and tetrabutylammonium hydrogen sulfate (60 mg, 0.177 mmol), using a similar process to that described in example 1. $^1$H NMR (CDCl$_3$) δ 10.23 (m, 1 H), 8.38 (s, 1 H), 7.31 (m, 1 H), 6.76 (m, 2 H), 5.98 (d, J=6.4 Hz, 1 H), 5.89 (d, J=6.4 Hz, 1 H), 4.72-4.53 (m, 5 H), 4.28 (m, 2 H), 4.15 (m, 1 H), 3.92 (m, 1 H), 3.73 (s, 3 H), 3.14-3.03 (m, 2 H), 2.82 (m, 1 H), 2.10-1.91 (m, 3 H), 1.68 (m, 1 H). ES$^+$ MS: 577 (M+1).

EXAMPLE 4

{[(4aS,13aR)-8-({[(2,4-Difluorophenyl)methyl]
amino}carbonyl)-9,11-dioxo-2,3,4a,5,9,11,13,13a-
octahydro-1H-pyrido[1,2-a]pyrrolo[1',2':3,4]imidazo
[1,2-d]pyrazin-10-yl]oxy}methyl 2-(4-morpholinyl)
ethyl carbonate formic acid salt.

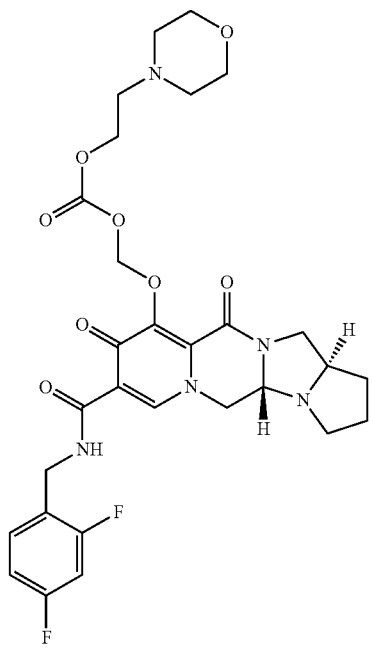

a) Chloromethyl 4-nitrophenyl carbonate. N-methyl morpholine (1.24 mL, 11.24 mmol) was added dropwise to a solution of 4-nitrophenol (1.56 g, 11.24 mmol) in dichloromethane at 0° C., followed by dropwise addition of chloromethyl chloridocarbonate (1 mL, 11.24 mmol) and the mixture was stirred for 14 hours at ambient temperature. The reaction was diluted with citric acid solution, extracted with dichloromethane, washed with aqueous sodium bicarbonate, brine, and dried over sodium sulfate to yield the title compound as a yellow oil. $^1$H NMR (CDCl$_3$) δ 8.29 (m, 2 H), 7.40 (m, 2 H), 5.82 (s, 2 H).

b) Iodomethyl 4-nitrophenyl carbonate. Chloromethyl 4-nitrophenyl carbonate (2.61 g, 10.63 mmol), sodium iodide (2.39 g, 15.94 mmol) were suspended in acetone and heated overnight at 45° C. The yellow suspension was allowed to cool to ambient temperature, concentrated under reduced pressure, diluted with water and aqueous sodium thiosulfate, extracted with dichloromethane, washed with brine, dried over sodium sulfate, and concentrated under reduced pressure to give the title compound as a clear yellow oil. $^1$H NMR (CDCl$_3$) δ 8.30 (dd, J=7.2, 2.4 Hz, 2 H), 7.42 (dd, J=6.8, 2 Hz, 2 H), 6.06 (s, 2 H).

c) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 4-nitrophenyl carbonate. The title compound was prepared from (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (500 mg, 1.11 mmol), 3.32 mmol), iodomethyl 4-nitrophenyl carbonate (excess), and tetrabutylammonium hydrogen sulfate (375 mg, 1.11 mmol) in a manner similar to that described in example 1, step c, to give an impure mixture of the title compound. $^1$H NMR (CDCl$_3$) δ 10.19 (m, 1 H), 8.42 (s, 1 H), 8.24 (m, 2 H), 7.53 (m, 2 H), 7.31 (m, 1 H), 6.78 (m, 2 H), 6.04 (d, J=6.4 Hz, 1 H), 5.97 (d, J=6.4 Hz, 1 H), 4.63-4.50 (m, 3 H), 4.30-4.16 (m, 2 H), 3.95-3.70 (m, 2 H), 3.15-3.03 (m, 2 H), 2.83 (m, 1 H), 2.09-1.88 (m, 3 H), 1.68 (m, 1 H). ES$^+$ MS: 626 (M+1).

d) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(4-morpholinyl)ethyl carbonate formic acid salt. The product prepared as described in step (c) above (200 mg, 0.320 mmol), 2-(4-morpholinyl)ethanol (0.04 mL, 0.320 mmol), DMAP (39 mg, 0.228 mmol), and triethylamine (0.13 mL, 0.959 mmol) in acetonitrile were stirred at reflux for 1 hour. The reaction was concentrated under reduced pressure, diluted with water, extracted with dichloromethane, washed with sodium bicarbonate solution, brine, and dired over sodium sulfate. Purification by reverse-phase HPLC yielded the title compound as the formic acid salt. $^1$H NMR (CDCl$_3$) δ 10.23 (m, 1 H), 8.42 (s, 1 H), 7.28 (m, 1 H), 6.75 (m, 2 H), 5.90 (d, J=6.4 Hz, 1 H), 5.78 (d, J=6.4 Hz, 1 H), 4.61-4.47 (m, 3 H), 4.34 (m, 2 H), 4.19 (m, 2 H), 3.86 (m, 1 H), 3.73-3.64 (m, 5 H), 3.11-2.99 (m, 2 H), 2.85-2.66 (m, 7 H), 2.07-1.82 (m, 3 H), 1.64 (m, 1 H). ES$^+$ MS: 618 (M+1).

EXAMPLE 5

{[(4aS,13aR)-8-({[(2,4-Difluorophenyl)methyl]
amino}carbonyl)-9,11-dioxo-2,3,4a,5,9,11,13,13a-
octahydro-1H-pyrido[1,2-a]pyrrolo[1',2':3,4]imidazo
[1,2-d]pyrazin-10-yl]oxy}methyl 2-hydroxyethyl
carbonate.

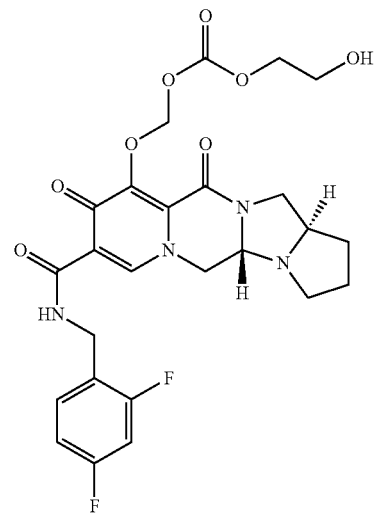

a) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-[(phenylmethyl)oxy]ethyl carbonate. The title compound was prepared in 40% yield according to example 1 from (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (2.00 g, 4.42 mmol), iodomethyl 2-[(phenylmethyl)oxy]ethyl carbonate (3.80 g, 11.3 mmol), potassium carbonate (1.83 g, 13.3 mmol) and tetrabutylammonium hydrogen sulfate (1.50 g, 4.42 mmol). $^1$H NMR (400 MHz, CHLOROFORM-d) δ ppm 10.24 (t, J=5.9 Hz, 1 H), 8.39 (s, 1 H), 7.35-7.20 (m, 6 H), 6.83-6.71 (m, 2 H), 5.93 (d, J=6.5 Hz, 1 H), 5.83 (d, J=6.5 Hz, 1 H), 4.60-4.54 (m, 2 H), 4.53 (s, 2 H), 4.47 (dd, J=10.6, 3.3 Hz, 1 H), 4.40-4.29 (m, 2 H), 4.20-4.09 (m, 2 H), 3.87-3.76 (m, 1 H), 3.71 (t, J=4.9 Hz, 2 H), 3.65-3.56 (m, 1 H), 3.12-3.03 (m, 1 H), 2.98 (dd, J=12.0, 7.2 Hz, 1 H), 2.81-2.72 (m, 1 H), 1.79-2.06 (m, 2 H), 1.52-1.72 (m, 2 H); ES$^+$ MS: 639 (M+1).

b) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-hydroxyethyl carbonate. A solution of the intermediate from step a (1.10 g, 1.72 mmol) in 40 mL of 1:1 methanol/acetic acid was subjected to hydrogenation at 50 psi in the presence of 0.50 g of 10% palladium on charcoal (Degussa type). After 18 hours the reaction vessel was purged with nitrogen, catalyst removed by filtration through celite, and the filtrate concentrated to dryness at reduced pressure. The residue was dissolved in 40 mL of dichloromethane and the solution mixed with an equal volume of saturated aqueous sodium bicarbonate. The mixture was stirred vigorously for 20 minutes and the phases separated. The aqueous phase was extracted with an additional portion of dichloromethane. The combined dichloromethane solutions were washed with saturated aqueous brine (1×), dried over sodium sulfate and concentrated to dryness at reduced pressure to afford the title compound (0.66 g, 70%) as a light tan foam. $^1$H NMR (400 MHz, CHLOROFORM-d) δ ppm 10.15 (t, J=5.7 Hz, 1 H), 8.41 (s, 1 H), 7.37-7.27 (m, 1 H), 6.84-6.73 (m, 2 H), 5.97 (d, J=6.8 Hz, 1 H), 5.89 (d, J=6.8 Hz, 1 H), 4.62-4.46 (m, 4 H), 4.23-4.12 (m, 3 H), 4.03-3.74 (m, 4 H), 3.74-3.63 (m, 1 H), 3.15-3.06 (m, 2 H), 2.85-2.74 (m, 1 H), 2.11-1.82 (m, 2 H), 1.71-1.57 (m, 2 H); ES$^+$ MS: 549 (M+1).

EXAMPLE 6

{[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(phosphonooxy)ethyl carbonate mono-sodium salt.

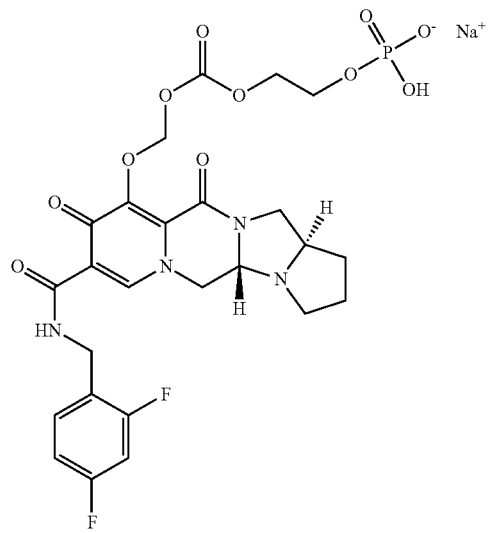

a) 2-({Bis[(phenylmethyl)oxy]phosphoryl}oxy)ethyl {[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl carbonate. To a stirred solution of {[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-hydroxyethyl carbonate (0.620 g, 1.13 mmol) and tetrazole (0.630 g, 9.04 mmol) in 20 mL of anhydrous dichloromethane was added dibenzyl N,N-diisopropyl phosphoramidite (1.56 g, 4.52 mmol). The resulting solution was stirred at RT. After 2.0 hours the solution was cooled in an ice water/brine bath. The solution was treated with m-CPBA (0.585 g, 3.39 mmol) added in small portions over a period of 2.5 hours. The solution was mixed with 40 mL of 10% aqueous sodium thiosulfate and the mixture stirred vigorously for a few minutes. The phases were separated and the aqueous solution extracted with an additional portion of dichloromethane. The combined dichloromethane solutions were washed with saturated aqueous sodium bicarbonate (1×), dried over sodium sulfate and concentrated to dryness at reduced pressure to afford a light yellow foam. This material was subjected to flash chromatography (silica gel, gradient elution from dichloromethane to 95:5 dichloromethane/methanol) to afford the title compound (0.61 g, 67%) as a light yellow foam. $^1$H NMR (400 MHz, CHLOROFORM-d) δ ppm 10.23 (t, J=5.8 Hz, 1 H), 8.30 (s, 1 H), 7.38-7.24 (m, 11 H), 6.83-6.72 (m, 2 H), 5.96 (d, J=6.6 Hz, 1 H), 5.87 (d, J=6.6 Hz, 1 H), 5.00 (t, J=7.9 Hz, 4 H), 4.66-4.51 (m, 2 H), 4.46-4.36 (m, 2 H), 4.35-4.15 (m, 4 H), 4.02 (dd, J=12.4, 2.8 Hz, 1 H), 3.79-3.59 (m, 2 H), 3.13-3.02 (m, 1 H), 2.95 (dd, J=12.0, 7.4 Hz, 1 H), 2.79-2.69 (m, 1 H), 2.05-1.78 (m, 2 H), 1.65-1.53 (m, 2 H); ES$^+$ MS: 809 (M+1).

b) {[(4aS,13aR)-8-({[(2,4-Difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 2-(phosphonooxy)ethyl carbonate mono-sodium salt. A solution of the intermediate from step a (0.610g, 0.754 mmol) in 40 mL of methanol was subjected to hydrogenation at 50 psi in the presence of 100 mg of 10% palladium on charcoal. After 4 hours a white solid had formed in the reaction mixture. The vessel was purged with nitrogen and the reaction progress assessed by LCMS which indicated primarily desired product with approximately 5% of the monobenzyl phosphate intermediate. The mixture was diluted with 20 mL of methanol, treated with an additional 50 mg of catalyst, and again subjected to 50 psi of hydrogen pressure. After an additional 1.5 hours LCMS indicated little or no change. The mixture was treated with 40 mL of water followed by sodium bicarbonate (63 mg, 0.754 mmol) to facilitate dissolution of the solid product and again subjected to hydrogenation at 50 psi. After 1 hour LCMS indicated complete reaction. The catalyst was removed by filtration through celite and the filtrate concentrated to dryness by rotary evaporation. The residue was triturated with methanol which induced precipitation of a white solid. The suspension was diluted with ether, stirred for 30 minutes and the solid collected by filtration and dried under vacuum. This afforded the title compound (0.438 g, 89%) as a white powder. $^1$H NMR (400 MHz, DEUTERIUM OXIDE) δ ppm 8.34 (s, 1 H), 7.24-7.14 (m, 1 H), 6.84-6.72 (m, 2 H), 5.65 (d, J=6.8 Hz, 1 H), 5.35 (d, J=6.8 Hz, 1 H), 4.69- 4.58 (m, 2 H), 4.47-4.34 (m, 2 H), 4.23-4.10 (m, 2 H), 4.06-3.90 (m, 2 H), 3.90-3.82 (m, 2 H), 3.69-3.60 (m, 1 H), 3.12 (dd, J=12.2, 6.8 Hz, 1 H), 2.99-2.88 (m, 1 H), 2.86-2.77 (m, 1 H), 1.98-1.84 (m, 2 H), 1.78-1.56 (m, 2 H); ES+ MS: 629 (M+1).

EXAMPLE 7

{[(4aS,13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo [1,2-d]pyrazin-10-yl]oxy}methyl 3-hydroxypropyl carbonate acetic acid salt.

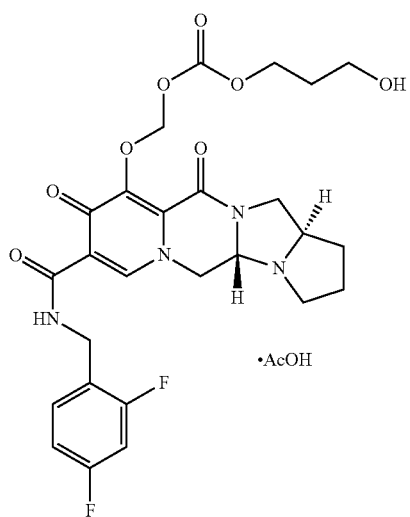

a) {[(4aS,13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-[(phenylmethyl)oxy] propyl carbonate. The title compound was prepared in 71% yield according to example 1 from (4aS,13aR)-N-[(2,4-difluorophenyl)methyl]-10-hydroxy-9,11-dioxo-2,3,4a,5,9,11,13,13a-octahydro-1H-pyrido[1,2-a]pyrrolo[1',2':3,4]imidazo[1,2-d]pyrazine-8-carboxamide sodium salt (1.00 g, 2.21 mmol), iodomethyl 2-[(phenylmethyl)oxy]propyl carbonate (3.15 g, 9.00 mmol), potassium carbonate (1.92 g, 13.9 mmol) and tetrabutylammonium hydrogen sulfate (1.25 g, 3.68 mmol). ¹H NMR (400 MHz, CHLOROFORM-d) δ ppm 10.23 (t, J=5.7 Hz, 1 H), 8.37 (s, 1 H), 7.36-7.21 (m, 6 H), 6.83-6.70 (m, 2 H), 5.91 (d, J=6.6 Hz, 1 H), 5.82 (d, J=6.5 Hz, 1 H), 4.64-4.39 (m, 5 H), 4.35-4.24 (m, 2 H), 4.24-4.08 (m, 2 H), 3.91-3.76 (m, 1 H), 3.70-3.59 (m, 1 H), 3.55 (t, J=6.2 Hz, 2 H), 3.16-3.04 (m, 1 H), 2.99 (dd, J=12.0, 7.2 Hz, 1 H), 2.84-2.72 (m, 1 H), 2.08-1.79 (m, 4 H), 1.69-1.53 (m, 2 H); ES+ MS: 653 (M+1).

b) {[(4aS,13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-hydroxypropyl carbonate acetic acid salt. A solution of the intermediate from step a (1.02 g, 1.56 mmol) in 50 mL of 1:1 AcOH/MeOH was subjected to hydrogenation at 55 psi in the presence of 1.0 g of 10% palladium on carbon (Degussa type). After 3 hours the reaction vessel was purged with nitrogen, catalyst removed by filtration through celite and the filtrate concentrated to dryness at reduced pressure. In order to remove the residual acetic acid, the residue was dissolved in methanol and concentrated to dryness twice. The resulting solid was dissolved in a minimum volume of methanol and the solution stirred with addition of ether which induced the formation of a light tan solid. The suspension was stirred at RT for 2 hours. The solid was collected by vacuum filtration and dried under vacuum to afford the title compound (0.68 g, 70%) as an off white powder. ¹H NMR (400 MHz, CHLOROFORM-d) δ ppm 10.25-10.15 (m, 1 H), 8.34 (s, 1 H), 7.32-7.19 (m, 1 H), 6.80-6.68 (m, 2 H), 5.82 (d, J=6.6 Hz, 1 H), 5.72 (d, J=6.6 Hz, 1 H), 4.72-3.71 (m, 9 H), 3.63 (t, J=5.9 Hz, 2 H), 3.27-2.71 (m, 6 H), 2.18-1.60 (m, 6 H); ES+ MS: 563 (M+1).

EXAMPLE 8

{[(4aS,13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo [1,2-d]pyrazin-10-yl]oxy}methyl 3-hydroxypropyl carbonate.

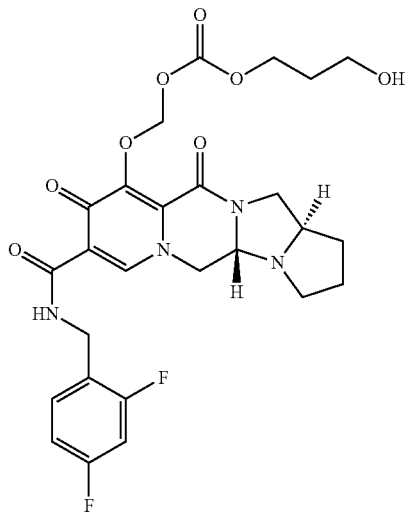

A solution of {[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d] pyrazin-10-yl]oxy}methyl 3-[(phenylmethyl)oxy] propyl carbonate (2.30 g, 3.52 mmol) in 50 mL of 1:1 MeOH/AcOH was subjected to hydrogenation at 55 psi in the presence of 0.75 g of 10% palladium on charcoal. After 5 hours the reaction vessel was purged with nitrogen, catalyst removed by filtration through celite and the filtrate concentrated to dryness at reduced pressure. The residue was dissolved in dichloromethane and the solution mixed with saturated aqueous sodium bicarbonate. The mixture was stirred vigorously for 25 minutes and the phases separated. The aqueous phase was extracted with one additional portion of dichloromethane. The combined dichloromethane solutions were washed with saturated aqueous brine, dried over sodium sulfate and concentrated to dryness at reduced pressure to give the title compound (1.96 g, 99%) as a light tan foam. ¹H NMR (400 MHz, CHLOROFORM-d) δ ppm 10.18 (t, J=5.8 Hz, 1 H), 8.39 (s, 1 H), 7.37-7.26 (m, 1 H), 6.84-6.72 (m, 2 H), 5.93 (d, J=6.6 Hz, 1 H), 5.85 (d, J=6.6 Hz, 1 H), 4.66-4.36 (m, 4 H), 4.34-4.10 (m, 3 H), 3.87 (t, J=11.3 Hz, 1 H), 3.79-3.64 (m, 3 H), 3.17-3.02 (m, 2 H), 2.90-2.74 (m, 2 H), 2.11-1.81 (m, 4 H), 1.71-1.57 (m, 2 H); ES+ MS: 563 (M+1).

EXAMPLE 9

{[(4aS,13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo [1,2-d]pyrazin-10-yl]oxy}methyl 3-(phosphonooxy) propyl carbonate mono-sodium salt.

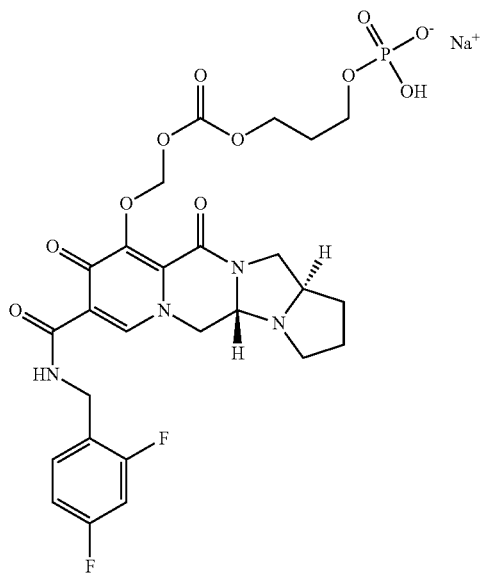

a) 3-({Bis[(phenylmethyl)oxy]phosphoryl}oxy)propyl {[(4aS,13aR)-8-({[(2,4-difluorophenyl)methyl] amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl carbonate. The title compound was prepared in 81% yield according to example 6 from {[(4aS,13aR)-8-({[(2,4-difluorophenyl)methyl]amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-hydroxypropyl carbonate (0.50 g, 0.889 mmol) using tetrazole (0.498 g, 7.11 mmol), dibenzyl N,N-diisopropyl phosphoramidite (1.23 g, 3.56 mmol) and m-CPBA (0.460 g, 2.67 mmol). $^1$H NMR (400 MHz, CHLOROFORM-d) δ ppm 10.22 (t, J=5.8 Hz, 1 H), 8.33 (s, 1 H), 7.37-7.24 (m, 11 H), 6.83-6.72 (m, 2 H), 5.93 (d, J=6.5 Hz, 1 H), 5.85 (d, J=6.6 Hz, 1 H), 5.06-4.93 (m, 4 H), 4.65-4.50 (m, 2 H), 4.48-4.37 (m, 1 H), 4.32-4.16 (m, 3 H), 4.16-4.02 (m, 3 H), 3.88-3.74 (m, 1 H), 3.73-3.60 (m, 1 H), 3.15-3.04 (m, 1 H), 2.98 (dd, J=11.9, 7.3 Hz, 1 H), 2.82-2.70 (m, 1 H), 2.09-1.78 (m, 4 H), 1.67-1.52 (m, 2 H); ES+ MS: 823 (M+1).

b) {[(4aS, 13aR)-8-({[(2,4-Difluorophenyl)methyl] amino}carbonyl)-9,11-dioxo-2,3,4a,5,9,11,13,13a-octahydro-1H-pyrido[1,2-a]pyrrolo[1',2':3,4]imidazo[1,2-d]pyrazin-10-yl]oxy}methyl 3-(phosphonooxy) propyl carbonate mono-sodium salt. A solution of the intermediate from step a (0.300 g, 0.365 mmol) in 35 mL of methanol was subjected to hydrogenation at 50 psi in the presence of 50 mg of 10% palladium on charcoal. After 1.5 hours a white solid had formed in the reaction mixture. The vessel was purged with nitrogen and the reaction progress assessed by LCMS which indicated a 1:1 mixture of desired product to mono-benzyl phosphate intermediate. The mixture was diluted with 25 mL of methanol, treated with an additional 50 mg of catalyst, and again subjected to 50 psi of hydrogen pressure. After 2 hours LCMS indicated complete reaction. The mixture (still containing catalyst) was transferred to a round bottomed flask, diluted with 50 mL of water, and treated with sodium bicarbonate (31 mg, 0.365 mmol). Rotary evaporation to half volume led to dissolution of the product. The catalyst was removed by filtration through celite and the filtrate concentrated to dryness at reduced pressure. The residue was suspended in methanol, stirred for a few minutes, and concentrated to dryness. This was repeated twice to afford the title compound (0.233 g, 96%) as an off-white powder. $^1$H NMR (400 MHz, DEUTERIUM OXIDE) δ ppm 8.33 (s, 1 H), 7.24-7.13 (m, 1 H), 6.85-6.70 (m, 2 H), 5.61 (d, J=6.8 Hz, 1 H), 5.34 (d, J=6.8 Hz, 1 H), 4.68-4.57 (m, 2 H), 4.47-4.33 (m, 2 H), 4.16-3.88 (m, 4 H), 3.78-3.58 (m, 3 H), 3.10 (dd, J=12.0, 6.6 Hz, 1 H), 2.99-2.88 (m, 1 H), 2.86-2.75 (m, 1 H), 2.00-1.54 (m, 6 H); ES+ MS: 643 (M+1).

EXAMPLE 10

Rat Pharmacokinetics

Fasted male CD rats received the compound of Example 2 as an oral suspension dose (5 mg parent equivalent/kg in 0.1% hydroxypropylmethylcellulose/0.1% Tween-80) administered via an oral gavage needle. Blood samples (0.2 mL each) were drawn from a surgically implanted femoral vein cannula at timed intervals for 24 h following dose administration; all samples were drawn using EDTA-treated syringes. Each blood sample was combined with 0.02 mL of a protease inhibitor solution [e-amino-n-caproic acid, benzamide HCl, and 4-(2-aminoethyl) benzenesulfonyl fluoride HCl in water] to inhibit ex vivo conversion of prodrug to parent, vortexed to mix, and centrifuged (4000× g, 4° C., 20 min) to harvest plasma. Prodrug and parent concentrations in plasma samples were quantitated by LC/MS/MS analysis. Area under the plasma concentration-time curve was estimated using non-compartmental analysis methods (WinNonlin Professional 4.1)

The invention claimed is:
1. A process for the preparation of a compound of formula 1b

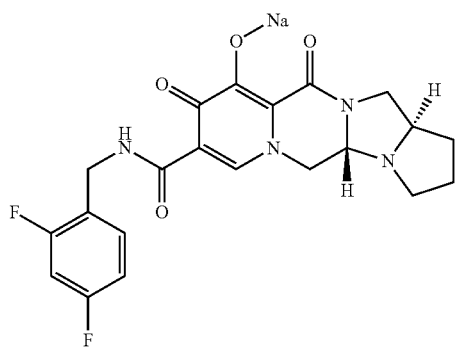

comprising the steps of:
a) brominating a compound of formula P-7

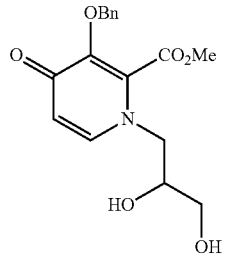
P-7 to form a compound of formula P-8

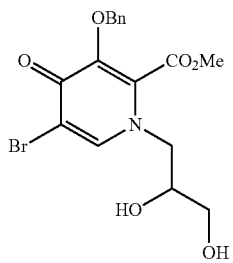
P-8 b) treating a compound of formula P-8 with NaIO$_4$ to form a compound of formula P-9

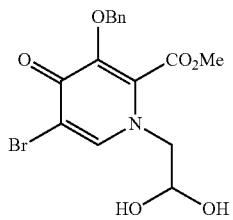
P-9 c) reacting a compound of formula P-9 with [(2R)-pyrrolidinylmethyl]amine of formula

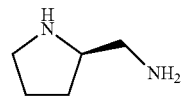

to form a compound of formula P-10

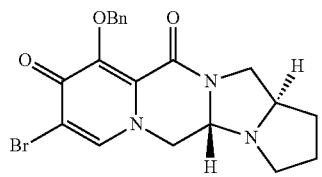
P-10 d) reacting a compound of formula P-10 with 2, 4-difluorobenzylamine to form a compound of formula P-11

P-11 e) treating a compound of P-11 with palladium on carbon and ammonium hydroxide to form a compound of formula 1a 1a f) treating a compound of formula 1a with NaOH and ethanol to form a compound of formula 1b.

* * * * *